United States Patent [19]

Gurgiolo

[11] Patent Number: 4,588,840

[45] Date of Patent: May 13, 1986

[54] OXYALKYLENE AROMATIC AMINES

[75] Inventor: Arthur E. Gurgiolo, Lake Jackson, Tex.

[73] Assignee: The Dow Chemical Company, Midland, Mich.

[21] Appl. No.: 654,717

[22] Filed: Sep. 27, 1984

Related U.S. Application Data

[63] Continuation-in-part of Ser. No. 371,765, Apr. 26, 1982, abandoned.

[51] Int. Cl.$^4$ .............................................. C07C 87/50
[52] U.S. Cl. ................................................... 564/443
[58] Field of Search ........................................ 564/443

[56] References Cited

U.S. PATENT DOCUMENTS

| | | | |
|---|---|---|---|
| 2,684,893 | 7/1954 | Hughes et al. | 564/443 X |
| 2,797,152 | 6/1957 | Hughes et al. | 564/443 X |
| 3,152,998 | 10/1964 | Moss | 252/470 |
| 3,347,926 | 10/1967 | Zech | 564/443 UX |
| 3,354,209 | 11/1967 | Brack | 564/443 |
| 3,654,370 | 4/1972 | Leakey | 564/443 UX |
| 4,101,690 | 7/1978 | Miyamoto et al. | 564/443 X |
| 4,145,367 | 3/1970 | Boozalis et al. | 564/443 UX |
| 4,152,353 | 5/1979 | Habermann | 564/443 UX |
| 4,153,581 | 5/1979 | Habermann | 252/472 |
| 4,301,083 | 11/1981 | Yoshimura et al. | 564/443 X |

Primary Examiner—Paul F. Shaver
Attorney, Agent, or Firm—Gary C. Cohn

[57] ABSTRACT

Polyoxyalkylaryl polyamines are prepared by reacting a polyoxyalkylene polyol with an aromatic amine in the presence of hydrogen and a catalyst containing Ni, Co, Cu or Mn.

8 Claims, No Drawings

OXYALKYLENE AROMATIC AMINES

CROSS REFERENCE TO RELATED APPLICATION

This is a continuation-in-part of copending application Ser. No. 371,765 filed Apr. 26, 1982, now abandoned.

BACKGROUND OF THE INVENTION

The present invention pertains to aromatic amines and their preparation.

Aminated polyglycols have been prepared in U.S. Pat. Nos. 3,654,370; 4,152,353 and 4,153,581 by reacting a polyglycol with ammonia in the presence of hydrogen and a catalyst.

The aminated polyols have high reactivity rates with organic isocycantes and in some instances are too reactive. The present invention provides for aminated polyols with reduced reactivity toward organic isocyanates.

SUMMARY OF THE INVENTION

The present invention concerns aromatic amines represented by the general formulas

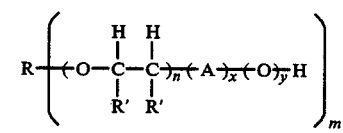

I.

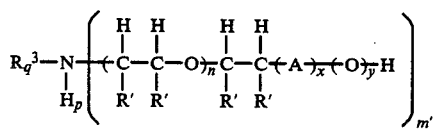

II.

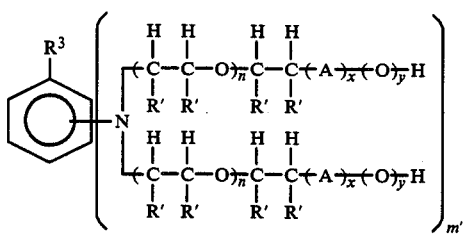

III.

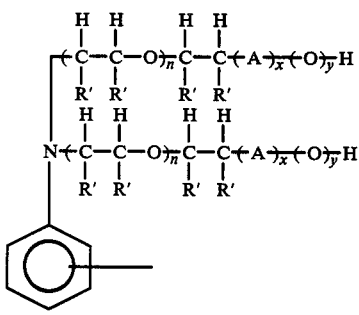

IV.

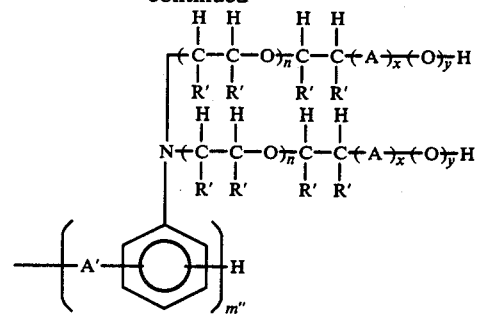

V.

wherein A is a divalent group represented by the formula $$\begin{array}{c} R'' \quad R'' \\ -N\text{—}\bigcirc \\ | \\ H \\ R'' \end{array}$$

;

A' is a divalent aliphatic hydrocarbyl group having from 1 to about 10 carbon atoms; A" is a divalent aliphatic hydrocarbon group having from 2 to about 10 carbon atoms; R is the residue which would result from the removal of the hydroxyl group(s) from a hydroxyl-containing compound having from 1 to about 8, preferably from 1 to about 4, hydroxyl groups per molecule; each R' is independently hydrogen, methyl, ethyl, propyl, butyl or phenyl with the proviso that within each $$\begin{array}{c} H \quad H \\ | \quad | \\ -C\text{—}C\text{—} \\ | \quad | \\ R' \quad R' \end{array}$$

group, at least one R' is hydrogen; each R" is independently hydrogen, a halo group or a hydrocarbon or hydrocarbyloxy group having from 1 to about 8, preferably from 1 to about 4, carbon atoms; $R^3$ is a hydrocarbon group having from 1 to about 8, preferably from 1 to about 4, carbon atoms; m has a value corresponding to the number of hydroxyl groups present in said hydroxyl-containing compounds; m' has a value of 1 or 2; m" has an average value from 1 to about 6; n has a value of from about 1 to about 200, preferably from about 2 to about 100; n' has a value of from zero to about 5; q is one or two provided that q plus m' does not exceed three; p has a value equal to 3 minus the sum of m' plus q; each x is independently zero or 1 with the proviso that within each formula at least one x has a value of 1; and y has a value of 1 when x is zero and a value of zero when x is 1.

The present invention also pertains to a process for preparing the oxyalkylene aromatic amines described above which process comprises reacting (A) at least 1 hydroxyl-containing compound represented by the general formulas

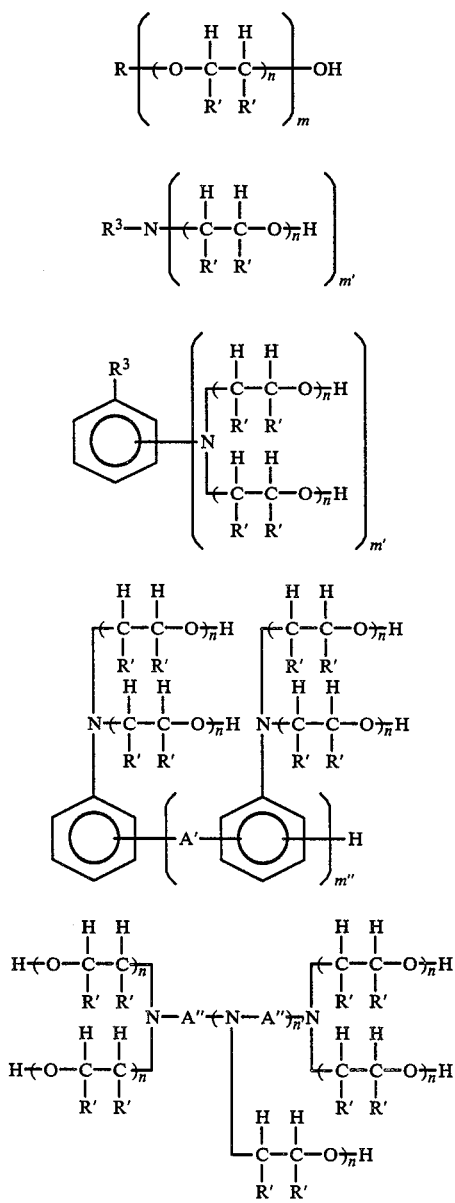

wherein A', A", R, R'; R³, m, m', m", n and n' are as described above with (B) at least one aromatic amine represented by the general formula

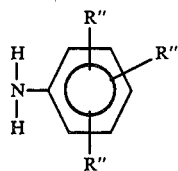

wherein R" is as defined above; in the presence of (C) hydrogen and (D) a catalyst containing nickel, copper, cobalt, manganese or mixtures thereof.

DETAILED DESCRIPTION OF THE INVENTION

Suitable hydroxyl-containing compounds which can be employed herein include those prepared by reacting an initiator compound having from about 1 to about 8 active hydrogen atoms per molecule with a vicinal epoxide.

Particularly suitable initiator compounds include, for example, water, ethylene glycol, propylene glycol, neopentyl glycol, dibromoneopentyl glycol, 1,4-butane diol, 1,3-butane diol, 1,6-hexane diol, glycerine, pentaerythritol, sucrose, mixtures thereof and the like. Also suitable are alcohols such as methanol, ethanol, propanol, butanol, octanol and the like. Suitable also are amines such as, for example, methyl amine, ethyl amine, aniline, substituted aniline, toluene diamine, methylene diphenylamine, polymethylene polyphenylamine, ethylenediamine, diethylenetriamine, triethylenetetramine, tetraethylenepentamine, mixtures thereof and the like.

Suitable vicinal epoxides include, for example, ethylene oxide, propylene oxide, 1,2-butylene oxide, 2,3-butylene oxide, styrene oxide, methyl glycidyl ether, ethyl glycidyl ether, octyl glycidyl ether, phenyl glycidyl ether, mixtures thereof and the like.

Suitable aromatic amines which can be employed herein include, for example, aniline, o-toluidine, m-toluidine, p-toluidine, o-anisidine, m-anisidine, p-anisidine, 2-ethyl-6-isopropyl aniline, mixtures thereof and the like.

Suitable catalysts which can be employed herein include nickel-containing, copper-containing, manganese-containing and cobalt-containing catalysts such as, for example, those disclosed in U.S. Pat. Nos. 3,152,998; 3,654,370; 4,014,933; 4,152,353 and 4,153,581 which are incorporated herein by reference.

Suitable manganese-containing catalysts include, for example, manganese dioxide, manganese dioxide supported on activated alumina, mixtures thereof and the like which are reduced during the reaction.

In the process of the present invention, the polyol and aromatic amine are employed in quantities which provide a ratio of $NH_2:OH$ of from about 0.1:1 to about 3:1, preferably from about 1.2:1 to about 1.5:1.

The quantity of catalyst employed is that amount necessary to promote the reaction, usually that amount which provides from about 0.5 to about 2 moles of Ni and/or Co per mole of hydroxyl in the polyol.

The reaction is conducted at a temperature of from about 150° C. to about 300° C., preferably from about 180° C. to about 280° C. and most preferably from about 200° C. to about 250° C.

The pressure employed is usually from about 1 psig to about 5000 psig (6.9 kPa–34474 kPa), preferably from about 100 psig to about 1000 psig (689.5 kPa–6894.8 kPa) and most preferably from about 100 psig to about 500 psig (689.5 kPa-3447.4 kPa).

The time is that time required to essentially complete the reaction at the particular temperature and pressure employed and the particular reactants employed. However, suitable times usually are from about 5 hours (18000 s) to about 48 hours (172800 s), preferably from about 5 hours (18000 s) to about 18 hours (64800 s) and most preferably from about 5 hours (18000 s) to about 12 hours.

The following examples are illustrative of the invention but are not to be construed as to limiting the scope thereof in any manner.

The following components were employed in the examples.

CATALYST A is a supported catalyst containing 50% nickel by weight in ⅛" (0.32 cm) extruded form commercially available from The Harshaw Chemical Company as Ni-3266 E ⅛", nickel catalyst. The catalyst has the following properties

| A.B.D. (average bulk density) = | 0.72–0.80 g/cm$^3$ |
| S.A. (surface area) = | 145 m$^2$/g |
| P.V. (pore volume) = | 0.52 cm$^3$/g |

CATALYST B is a reduced and stabilized, non-pyrophoric powdered catalyst containing 60 weight percent nickel on kieselguhr having a ratio of reduced nickel to total nickel of 0.6, commercially available from The Harshaw Chemical Company as Ni-0104P spec. 104, nickel catalyst. The catalyst has the following properties.

| A.B.D = | 0.6 g/cm$^3$ |
| S.A. = | 100–125 m$^2$/g |
| P.V. = | 0.4 cm$^3$/g |

CATALYST C is a reduced and stabilized ⅛" (0.32 cm) tableted catalyst on a proprietary support containing 35 weight percent nickel commercially available from The Harshaw Chemical Company as Ni-3210T ⅛", nickel catalyst. The catalyst has the following properties.

| A.B.D. = | 0.88–0.95 g/cm$^3$ |
| Strength = | 9.0–22.7 kg |
| S.A. = | 125 m$^2$/g |
| P.V. = | 0.35 cm$^3$/g |

CATALYST D is a 3/16" (0.48 cm) reduced and stabilized tableted catalyst containing 50 weight percent nickel on a proprietary support commercially available from The Harshaw Chemical Company as Ni-3250T 3/16", nickel catalyst. The catalyst has the following properties.

| A.B.D. = | 1.02–1.09 g/cm$^3$ |
| Strength = | 6.8–11.35 kg |
| S.A. = | 150 m$^2$/g |
| P.V. = | 0.34 cm$^3$/g |

CATALYST E is a reduced, stabilized and non-pyrophoric powdered catalyst containing 65 weight percent nickel on a proprietary support commercially available from The Harshaw Chemical Company as Ni-5132P, nickel catalyst. The catalyst has the following properties.

| A.B.D. = | 0.45 g/cm$^3$ |
| S.A. = | 190 m$^2$/g |
| P.V. = | 0.32 cm$^3$/g |

CATALYST F is a zirconium dioxide supported powdered catalyst containing 50 mole percent cobalt and 45 weight percent copper and 5 mole percent ZrO$_2$ prepared in the following manner.

A 0.5 molar solution of Co(NO$_3$)$_2$·6H$_2$O was made by dissolving 145.5 g of crystals to one liter with distilled water.

A 0.45 molar solution of Cu(NO$_3$)$_2$·2½H$_2$O was made by dissolving 105 g of crystals to one liter with distilled water.

Two liters of 0.5 molar ammonium carbonate solution were made by dissolving 96 g solids to 2 liters of distilled water.

The Co and Cu solutions were mixed and 0.05 moles of ZrO$_2$ powder, 6.2 g, was suspended in mixed solutions.

With vigorous stirring, the two liters of 0.8 M ammonium carbonate solution was slowly added thus precipitating the corresponding cobalt carbonates and copper carbonates admixed with the ZrO$_2$.

The mixed precipitate was filtered, washed free of nitrate ions and dried at 60° C.

The dried carbonate mixture was then calcined to the corresponding Co-Cu-Zr oxide at 250° C. for one hour.

The product was screened to remove any lumps.

CATALYST G was a reduced stabilized non-pyrophoric ⅛" (0.32 cm) catalyst in tablet form containing 60 weight percent nickel commercially available from The Harshaw Chemical Company as Ni-0104T ⅛", nickel catalyst.

CATALYST H was a reduced and stabilized catalyst on a proprietary support in 3/16" (0.48 cm) tablet form containing 65% nickel commercially available from The Harshaw Chemical Company as Ni-5124 T 3/16" catalyst.

CATALYST I was a catalyst containing 3 to 4% each of nickel oxide, cobalt oxide, and iron oxide supported on activated alumina commercially available from Harshaw Chemical Company as Ni-1601 T ⅛", nickel catalyst.

CATALYST J was a supported catalyst containing 50% nickel by weight in 1/32" (0.08 cm) extruded form commercially available from The Harshaw Chemical Company as Ni 3226E 1/32", nickel catalyst.

CATALYST K was a supported catalyst containing 50 percent nickel by weight in ⅛" (0.32 cm) tablet form commercially available from the Harshaw Chemical Company as Ni-3266T ⅛" nickel catalyst.

CATALYST L was a powdered cobalt oxide prepared by heating an evaporating dish containing 60 grams (½ mole) of cobalt carbonate in a muffle furnace at 275° C. for 6 hours after which 38 grams of cobalt oxide was recovered.

CATALYST M was powdered manganese dioxide.

CATALYST N was powdered nickel oxide.

EXAMPLES 1–14

These examples employed the following general procedure.

A 70 ml stainless steel reactor was fitted with a screw cap and sealed by means of a Teflon O-ring. On the cap was mounted a 1000 psi (6895 kPa) pressure gage, a Hoke valve and a pressure relief valve set to relieve pressure at 750 psi (5171 kPa). These were connected by means of ¼" (0.635 cm) stainless steel tubing.

In these examples, 40 grams (0.1 mole of polyol or 0.2 mole of hydroxyl) of a polyoxypropylene glycol having an average molecular weight of about 400 (hereinafter referred to as P-400) was charged to the reactor. Then 20 grams (0.215 mole) of aniline was added and mixed. Then the catalyst was added and mixed. The type and amount of catalyst is indicated in Table I. The reactor was then sealed via the screw cap and O-ring. The system was then purged with hydrogen gas from a cylinder by evacuating the system and relieving the vacuum with hydrogen to 50 psi (345 kPa). This was done three times. Then the system was filled with hydrogen to a pressure indicated in Table I. The system was weighed before and after reaction as a routine check for any loss of reactants due to an inadvertant leak.

The system was then suspended in a fluidized sand bath, electrically heated and controlled at the temperature indicated in Table I.

The reactants were thus heated for the time indicated in Table I. They were intermittantly shaken manually. The reactor was removed from the hot sand bath and cooled in running water and then weighed to determine if any product was lost due to a leak. The pressure was released by means of the Hoke valve, and the reactor opened.

The product was analyzed for residual aniline by GPC analysis using a calibration curve made using pure aniline and adding a known amount of toluene as an internal standard. The percent aniline consumed was thus readily calculated and indicated in Table I.

The reactor was heated at 200° C. in a fluidized sand bath for 24 hours (86400 s). The pressure during reaction was 500 psig (3.4 MPa). The reactor was then cooled and the contents of each vial analyzed for percent aniline consumed. The catalysts employed and results are reported in Table II.

TABLE II

| EXAMPLE NO. | CATALYST TYPE/g | ANILINE CONSUMED % |
|---|---|---|
| 15 | F/1 | 69.8 |
| 16 | K/1 | 80.0 |
| 17 | E/1 | 75.5 |
| 18 | L/1 | 47.9 |
| 19 | M/1 | 47.8 |
| 20 | N/1 | 40.2 |

EXAMPLE 21

A 500 ml, 3 neck vessel was equipped with a stirrer, thermometer, hydrogen inlet, and Dean-Stark trap assembly filled with aniline. In the vessel was placed 200 grams (1 mole OH) of P-400 and 100 grams (1.074 moles) of aniline and 100 grams of Catalyst A (50% Ni). With stirring and with a slow stream of hydrogen passing through the reactants, the system was heated to 150° C. and allowed to react for 22 hours (79200 s). During this time an aniline-water azeotrope distilled over into the Dean Stark trap where the water separated out and a total of 28 grams water was recovered. The catalyst at 0.85 mole Ni will produce 15.3 grams of water and at 100% reaction 18 grams of water or a total of 33.3 grams will result so reaction was 84% complete. Analysis of the reaction product showed 82.3% of the aniline had been consumed. Since there was present 7 grams aniline in excess of theory, then 95.9% of the P-400 was capped.

TABLE I

| EXAMPLE NO. | CATALYST type/g | HYDROGEN PRESSURE psig/mpa | REACTION CONDITIONS | | | ANILINE CONSUMED wt. % |
|---|---|---|---|---|---|---|
| | | | TEMP. °C. | PRESSURE psig/MPA | TIME hrs./secs. | |
| 1 | A/10 | 50/0.34 | 200 | 200/1.38 | 8/28800 | 44.8 |
| 2 | A/10 | 150/1.03 | 200 | 250/1.72 | 5/18000 | 39.7 |
| 3 | A/20 | 500/3.45 | 150 | 740/5.1 | 47/169200 | 81.4 |
| 4 | B/10 | 350/2.41 | 200 | 500/3.45 | 24/86400 | 49.2 |
| 5 | G/10 | 350/2.41 | 200 | 500/3.45 | 24/86400 | 54.9 |
| 6 | C/10 | 350/2.41 | 200 | 500/3.45 | 24/86400 | 49.7 |
| 7 | D/10 | 350/2.41 | 200 | 500/3.45 | 24/86400 | 59.7 |
| 8 | H/10 | 350/2.41 | 200 | 500/3.45 | 24/86400 | 52.0 |
| 9 | E/10 | 350/2.41 | 200 | 500/3.45 | 24/86400 | 50.8 |
| 10 | A/10 | 350/2.41 | 200 | 500/3.45 | 24/86400 | 54.2 |
| 11 | F/10 | 350/2.41 | 200 | 500/3.45 | 24/86400 | 24.2 |
| 12 | I/30 | 350/3.41 | 200 | 500/3.45 | 24/86400 | 36.2 |
| 13 | J/30 | 350/2.41 | 200 | 500/3.45 | 24/86400 | 64 |
| 14 | A/30 | 350/2.41 | 200 | 500/3.45 | 24/86400 | 67.1 |

EXAMPLES 15–20

Into a plurality of wide mouth vials (16×40 mm) were weighed different catalysts as listed in Table II, one catalyst per vial. Separately, 40 grams (0.2 mole OH) of P-400 and 20 grams (1.215 mole) of aniline were weighed and mixed. Then 3 grams of this mixture were weighed into each vial containing catalyst so that each vial contained 2 grams (0.02 mole OH) of P-400 and 1 gram (0.0107 mole) of aniline. The vials were placed into a 70 ml stainless steel reactor and sealed. The system was purged with hydrogen and hydrogen added to a pressure of 300 psig (2 MPa).

EXAMPLE 22

A 500 ml 3 neck vessel was equipped with a stirrer, thermometer, hydrogen inlet, and a Dean-Stark trap assembly filled with aniline. In the vessel was placed 200 grams (1 mole OH) of P-400 and 100 grams (1.07) moles of aniline and 25 grams of Catalyst E, (65% Ni), (16 grams Ni) (0.2725 mole Ni will produce 5 grams water on reduction). The mixture was heated to 158° C. for 11 hours (39600 s) with a slow stream of hydrogen passing through. At this time 7.5 ml of water was recovered in the Dean-Stark trap and analysis shows 22% of the orginal aniline had reacted. The reaction was now continued for 5 hours (18000 s) more, all at 170° C. 13 grams more of water was recovered or 21 ml total. Analysis shows 84.4% of the original aniline had reacted and since there was 7 grams excess aniline present, then 91% capping occurred.

EXAMPLE 23

A 500 ml 3 neck vessel was equipped with a stirrer, thermometer, H$_2$ inlet and Dean-Stark trap assembly filled with aniline. In the vessel was placed 192 grams (2 mole OH) of tripropylene glycol (TPG) and 205 grams (2.2 moles) of aniline and 30 grams of Catalyst J was added (50% NiO or 15 grams Ni or 0.255 mole Ni and producing 4.6 grams H$_2$O). The mixture was heated and stirred and hydrogen gas slowly passed through the mixture. The temperature was allowed to slowly reach 184° C. over an 8 hour (18800 s) period. Only 0.25 ml of water was recovered. The next day the reaction was continued at 178°-204° C. for 5 hours (1800 s). 18 ml of water was recovered and analysis indicated 55% of the aniline had reacted. Also, 3.8% diphenylamine was found to be present as a by-product. The next day the reaction mixture was heated to 260° C. and 18 ml more of water was driven off, and all the aniline left was also allowed to distill off which was 36 ml. The percent conversion was 88%. The final product contained 5.8% diphenylamine. It was a dark viscous syrup after filtering and removing residual aniline.

EXAMPLE 24

A 500 ml 3 neck vessel was equipped with a stirrer, thermometer, hydrogen inlet and a Dean-Stark assembly. In the vessel was placed 150 grams (2 moles of OH) of triethylene glycol and 205 grams (2.2 moles) of aniline and 30 grams of Catalyst J (50% NiO or 15 grams Ni or 0.255 moles Ni which on reduction gives 4.6 grams H$_2$O). The mixture was stirred and heated to 196° C. for three hours (10800 s) with H$_2$ gas slowly passing through the mixture. Two ml of water was recovered. The next day the reaction was continued for 7 hours at 170°-250° C. The total water recovered for the 10 hours was 34 ml. Theory water was 36 grams +4.6—40.6 grams. Percent conversion equals 83.7%. The product was a dark viscous syrup after filtering and removing residual aniline.

EXAMPLE 25

A 5 neck, 2 liter vessel was equipped with a stirrer, thermometer, fritted tube, hydrogen, gas inlet tube, and a Dean-Stark trap assembly filled with aniline. In the vessel was placed 930 grams (4.84 moles) of tripropylyene glycol (TPG) (9.6 moles of OH) and 902 grams (9.69 moles) of aniline and 25 grams of catalyst J. The mixture was heated and stirred with a slow flow of hydrogen gas through the fritted tube. The inlet temperature was 200° C. The following reaction history describes this process.

| DAY NO. | CATALYST (g) | TEMP. °C. | REACTION TIME Hrs/Secs | WATER REMOVED (ml) | MOLES WATER REMOVED |
|---|---|---|---|---|---|
| 1 | 25 | 200 | 5.5/19800 | 6 | 0.33 |
| 2 | — | 180-190 | 6.5/23400 | 21 | 1.17 |
| 3 | 25 | 200 | 3.5/12600 | 63 | 3.50 |
| 4 | 25 | 200-230 | 7.0/25200 | 74 | 4.11 |
| 5 | — | 250 | 5.0/18000 | 4 | 0.22 |

Total Water=168 ml (9.33 moles)=92% of theory. Theory Water=9.675 moles×18=174 ml+0.5 moles or 9 grams from the catalyst=183 ml 10.17 moles. Recovered 1085 grams of filtered product after stripping off volatiles.

Analysis: Theory total nitrogen=8.234%; found 7.00%. Percent yield=85%. Theory tertiary nitrogen=0%; found 0.44%. The tertiary nitrogen would result if some of the product NH-φ groups reacted with a little TPG hydroxyls to give a coupled product. As can be seen, very little coupling occurred, which is unlike primary aminated polyglycols wherein considerable coupling occurs unless a large excess of ammonia is used to reduce the coupling side reaction. The product was a clear viscous syrup.

EXAMPLE 26

A 2 liter, 3 neck vessel was equipped with a stirrer, thermometer, fritted hydrogen gas inlet tube and Dean-Stark trap assembly. In the vessel was placed 1000 grams of P-400 (5 moles of hydroxyl) and 500 grams (5.37 moles) of aniline, and 75 grams of Catalyst E. The mixture was stirred and heated with a slow stream of hydrogen passing through the mixture. The temperature was slowly increased to 225° C. over a four hour (14400 s) period during which time 78 ml of water was collected in the Dean-Stark trap. Then 25 grams (0.67 moles) of aniline was added and the reaction continued for another hour (3600 s). At this time, 97 ml of water had collected in total. The theory amount of water for this reaction would be 90 ml from the polyol reaction and 9 ml from the catalyst or 99 ml. Therefore, based on the water produced, the reaction was 98% complete. The residual aniline was removed under reduced pressure and the product filtered. There was recovered 1271 grams of viscous light yellow oil. Analysis shows that 2.9% diphenylamine was present.

Analysis: Total nitrogen: Theory, 5.1%; found 4.6%. Secondary amine N: Theory, 5.1%, found 4.2%. Tertiary amine N: Theory, 0%, found 0.2%

NMR analysis: Theory % combines aniline=33.8%, found by NMR 30.5%.

% Yield=90.2%.

EXAMPLE 27

A 2 liter, 5 neck vessel was equipped with a stirrer, thermometer, fritted hydrogen gas inlet tube an Dean-Stark trap assembly. In the vessel was put 1000 grams (0.622 mole of OH) of a glycerine initiated polyoxypropylene glycol end-capped with about 50 weight percent ethylene oxide having an average OH equivalent weight of about 2607, 100 grams (1.074 moles) of aniline and 75 grams of Catalyst E. This mixture was stirred and heated to 248° C. with a slow stream of hydrogen passing through. After four hours (14400 s), 16 mls of water had collected in the trap and the reaction was terminated. The theoretical amount of water would be 11 ml from the polyol reaction and 9 ml by reduction of the NiO or 20 ml. So, based on water recovery, the reaction was 80% complete. NMR analysis: Theory % combined aniline=5.66%. Found by NMR, 3.3% % Yield=58.3%. The product was flashed and filtered before analysis.

EXAMPLE 28

Into a 70 ml reactor were charged:
40 grams (0.2 mole OH) of P-400
25 grams (0.233 mole) of p-toluidine 10 grams of Catalyst E These reactants were mixed and the reactor sealed. The system was then purged with hydrogen, then hydrogen added to 250 psig (1.72 MPa) pressure. The reactor and contents were then heated to 250° C. in a fluidized sand bath for 6 hours (21600 s). Then the system was cooled and the contents analyzed. It was found that 57.4% of the p-toluidine had reacted.

EXAMPLE 29

Into a 70 ml reactor were charged:
40 grams (0.2 mole OH) of P-400
25 grams (0.233 mole) of p-anisidine
10 grams of Catalyst E The reactants were mixed and the vessel sealed. The system was purged with hydrogen then pressurized with hydrogen to 250 psig (1.72 MPa). The reactor and contents were then heated to 250° C. in a fluidized sand bath for 17 hours (61200 s). After cooling the reactor contents were analyzed. It was found that 61.4% of the original p-anisidine had reacted.

EXAMPLE 30

Into a 70 ml reactor were charged:
46 g (0.1 mole OH) of a butanol initiated polyoxybutylene glycol having an average molecular weight of about 457 (% OH = ~3.72)
10 g (0.107 mole) aniline
5 g Catalyst B The reactants were mixed and the reactor sealed. The system was purged with hydrogen then pressurized with hydrogen to 350 psig (2.41 MPa). The reactor and contents were then heated to 250° C. in a fluidized sand bath for 54 hours (194400 s) with intermittent shaking. After cooling, the contents were analyzed. It was found that 50% of the aniline had been consumed.

EXAMPLE 31

To a stainless steel reactor were charged:
36 g (0.1 mole OH) of a butanol initiated polyoxybutylene glycol having an average MW of about 720 (% OH = ~4.72)
10 g (0.107 mole) of aniline
10 g Catalyst E These reactants were mixed and the reactor sealed. The system was then purged with hydrogen, then hydrogen added to 350 psig (2.41 MPa). The reactor and contents were then heated to 250° C. in a fluidized sand bath for 54 hours (194400 s) with intermittent shaking. The system was cooled and the contents analyzed. It was found that 73% of the aniline had been consumed.

EXAMPLE 32

A 5 liter 5 neck vessel was equpped with stirrer, thermometer, fritted glass hydrogen inlet tube, a Dean-Stark trap assembly and a heating mantle. In the vessel was placed 2350 g of a polyol, said polyol being glycerine initiated polyol prepared from a mixture of 17 weight percent ethylene oxide and 83 weight percent propylene oxide. The polyol has a % OH of 1.642 and an average molecular weight of 3100. The 53 g of aniline (0.57 moles) and 40 g of catalyst E was added. $H_2$ gas was introduced and the contents were heated to 225° C. with stirring. After 4 hours (14400 s) 15 ml of water was collected (theory from polyol was 10.3 ml). Then 25 g more of aniline (total = 0.84 moles) was added and the reaction was continued for 4 more hours (14400 s) and unreacted aniline was distilled out, of which there was 15 g. Total water recovered was 25 ml. Total aniline reacted was 63 g or 0.68 moles. No residual aniline was seen by gel permeation chromatograph. On this basis, 30% of the original OH content was reacted. Theory % nitrogen 0.43; found, 0.38%.

I claim:

1. Aromatic amines represented by the general formulas $$\text{I.} \quad R \left[ \left( O - \underset{R'}{\underset{|}{\overset{H}{\overset{|}{C}}}} - \underset{R'}{\underset{|}{\overset{H}{\overset{|}{C}}}} \right)_{\!n} (A)_x (O)_y H \right]_m$$

$$\text{II.} \quad R_q^3 - N \left[ \left( \underset{R'}{\underset{|}{\overset{H}{\overset{|}{C}}}} - \underset{R'}{\underset{|}{\overset{H}{\overset{|}{C}}}} - O \right)_{\!n} \underset{R'}{\underset{|}{\overset{H}{\overset{|}{C}}}} - \underset{R'}{\underset{|}{\overset{H}{\overset{|}{C}}}} (A)_x (O)_y H \right]_{m'} H_p$$

III. (structure with $R^3$-substituted phenyl ring bonded to N with two $\left[ \left( \underset{R'}{\underset{|}{\overset{H}{\overset{|}{C}}}} - \underset{R'}{\underset{|}{\overset{H}{\overset{|}{C}}}} - O \right)_{\!n} \underset{R'}{\underset{|}{\overset{H}{\overset{|}{C}}}} - \underset{R'}{\underset{|}{\overset{H}{\overset{|}{C}}}} (A)_x (O)_y H \right]_{m'}$ chains)

IV. (phenyl ring with two N-substituents each bearing two $\left( \underset{R'}{\underset{|}{\overset{H}{\overset{|}{C}}}} - \underset{R'}{\underset{|}{\overset{H}{\overset{|}{C}}}} - O \right)_{\!n} \underset{R'}{\underset{|}{\overset{H}{\overset{|}{C}}}} - \underset{R'}{\underset{|}{\overset{H}{\overset{|}{C}}}} (A)_x (O)_y H$ chains, connected via $(A')_{m''}$)

$$\text{V.} \quad H (O)_y (A)_x \underset{R'}{\underset{|}{\overset{H}{\overset{|}{C}}}} - \underset{R'}{\underset{|}{\overset{H}{\overset{|}{C}}}} \left( O - \underset{R'}{\underset{|}{\overset{H}{\overset{|}{C}}}} - \underset{R'}{\underset{|}{\overset{H}{\overset{|}{C}}}} \right)_{\!n} \!\!\!\diagdown\!\!\! N -$$
$$H (O)_y (A)_x \underset{R'}{\underset{|}{\overset{H}{\overset{|}{C}}}} - \underset{R'}{\underset{|}{\overset{H}{\overset{|}{C}}}} \left( O - \underset{R'}{\underset{|}{\overset{H}{\overset{|}{C}}}} - \underset{R'}{\underset{|}{\overset{H}{\overset{|}{C}}}} \right)_{\!n} \!\!\!\diagup$$

-continued

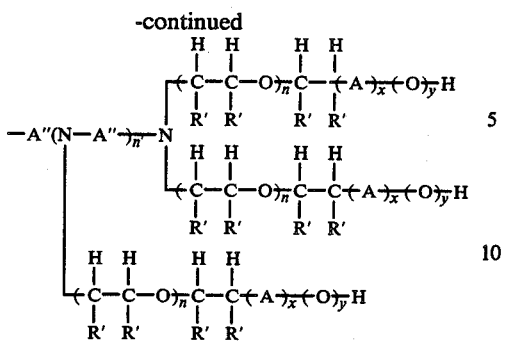

wherein A is a divalent group represented by the formula

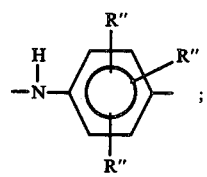

A' is a divalent aliphatic hydrocarbyl group having from 1 to about 10 carbon atoms; A" is a divalent aliphatic hydrocarbyl group having from 2 to about 10 carbon atoms; R is the residue which would result from the removal of the hydroxyl group(s) from a hydroxyl-containing compound having from 1 to about 8 hydroxyl groups per molecule; each R' is independently hydrogen, methyl, ethyl, propyl, butyl or phenyl with the proviso that within each

group, at least one R' is hydrogen; each R" is independently hydrogen, a halo group, a hydrocarbon or a hydrocarbyloxy group having from 1 to about 8 carbon atoms; $R^3$ is a hydrocarbon group having from 1 to about 8 carbon atoms; m has a value corresponding to the number of hydroxyl groups present in said hydroxyl-containing compound; m' has a value of 1 or 2; m" has an average value of from 1 to about 6; n has a value of from about one to about 200; n' has a value from zero to about 5; q is one or two provided that q plus m' does not exceed three; p has a value equal to 3 minus the sum of m' plus q; each x is independently zero or 1 with the proviso that within each formula at least one x has a value of 1; and y has a value of 1 when x is zero and a value of zero when x is 1.

2. Aromatic amines of claim 1 wherein R is the residue of a compound having from 1 to about 4 hydroxyl groups per molecule; each R" is independently hydrogen or a hydrocarbon or a hydrocarbyloxy group having from 1 to about 4 carbon atoms; $R^3$ has from 1 to about 4 carbon atoms; n has a value from about 1 to about 100; n' has a value of zero and m has a value of from about 1 to about 4.

3. Aromatic amines of claims 1 or 2 wherein each R" is hydrogen.

4. Aromatic amines of claims 1 or 2 wherein two of the R" groups are hydrogen and the other is a methyl or methoxy group.

5. A process for preparing oxyalkylene aromatic amines which comprises reacting
(A) at least one hydroxyl-containing compound represented by the general formulas

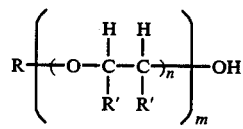   VI.

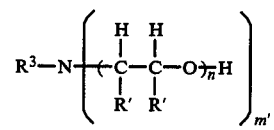   VII.

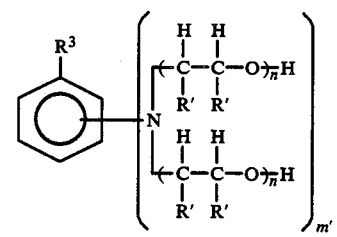   VIII.

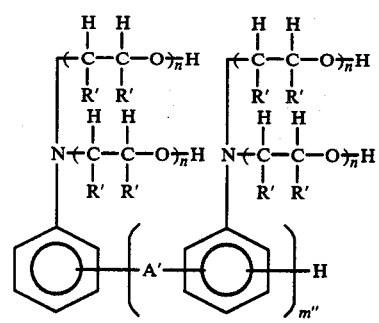   IX.

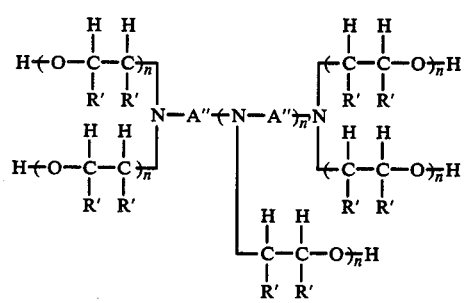   X.

wherein A' is a divalent aliphatic hydrocarbyl group having from 1 to about 10 carbon atoms; A" is a divalent aliphatic hydrocarbyl group having from 2 to about 10 carbon atoms; R is the residue which would result from the removal of the hydroxyl group(s) from a hydroxyl-containing compound having from 1 to about 8 hydroxyl groups per molecule; each R' is independently hydrogen, methyl, ethyl, propyl, butyl or phenyl with the proviso that within each

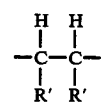

group, at least one R' is hydrogen; each R" is independently hydrogen, a halo group or a hydrocarbon or hydrocarbyloxy group having from 1 to about 8 carbon atoms; m has a value corresponding to the number of hydroxyl group(s) present in said hydroxyl-containing compound; m' has a value of 1 or 2; m" has an average value of from 1 to about 6; n has a value of from about 1 to about 200 and n' has a value from zero to about 5 with (B) at least one aromatic amine represented by the general formula

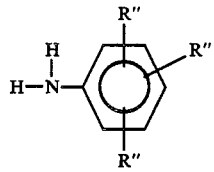

wherein each R" is independently hydrogen, a halo group or a hydrocarbon or hydrocaryloxy group having from 1 to about 8 carbon atoms; in the presence of (C) hydrogen; and (D) a catalyst containing nickel, copper, cobalt, manganese or mixtures thereof.

6. A process of claim 5 wherein R is the residue of a compound having from 1 to about 4 hydroxyl groups per molecule; each R" is independently hydrogen or a hydrocarbon group having from 1 to about 4 carbon atoms; $R^3$ has from 1 to about 4 carbon atoms; m has a value of from about 1 to about 4; n has a value from about 2 to about 100 and n' has a value of zero.

7. A process of claims 5 or 6 wherein each R" is hydrogen.

8. A process of claims 5 or 6 wherein two of the R" groups are hydrogen and the other is a methoxy or methyl group.

* * * * *